US008748615B2

(12) United States Patent
Elenbaas et al.

(10) Patent No.: US 8,748,615 B2
(45) Date of Patent: Jun. 10, 2014

(54) PROCESS FOR THE PREPARATION OF 2-(CYCLOHEXYLMETHYL)-N-{2-[(2S)-1-METHYLPYRROLIDIN-2-YL]ETHYL}-1,2,3,4-TETRAHYDROISOQUINOLINE-7-SULFONAMIDE

(75) Inventors: Steven Elenbaas, Bridgewater, NJ (US); Robert Allan Farr, Annadale, NJ (US); John Michael Kane, Bridgewater, NJ (US)

(73) Assignee: Sanofi, Paris (FR)

( * ) Notice: Subject to any disclaimer, the term of this patent is extended or adjusted under 35 U.S.C. 154(b) by 47 days.

(21) Appl. No.: 13/553,455

(22) Filed: Jul. 19, 2012

(65) Prior Publication Data

US 2013/0123302 A1 May 16, 2013

Related U.S. Application Data

(63) Continuation of application No. PCT/US2011/027131, filed on Mar. 4, 2011.

(60) Provisional application No. 61/311,069, filed on Mar. 5, 2010.

(30) Foreign Application Priority Data

Nov. 25, 2010 (FR) ...................................... 10 59750

(51) Int. Cl.
*C07D 401/12* (2006.01)

(52) U.S. Cl.
USPC ........................................................ 546/150

(58) Field of Classification Search
None
See application file for complete search history.

(56) References Cited

U.S. PATENT DOCUMENTS

| | | | |
|---|---|---|---|
| 4,228,170 A | 10/1980 | Bondinell et al. |
| 4,315,935 A | 2/1982 | Ali |
| 4,857,301 A | 8/1989 | Czarniecki et al. |
| 5,750,520 A | 5/1998 | Danilewicz et al. |
| 6,414,149 B1 | 7/2002 | Chu-Moyer et al. |
| 6,562,828 B1 | 5/2003 | Katoh et al. |
| 6,562,978 B1 | 5/2003 | Imamura et al. |
| 6,677,349 B1 | 1/2004 | Griesgraber |
| 7,833,999 B2 | 11/2010 | Diaz Martin et al. |
| 7,858,619 B2 | 12/2010 | Hofmeister et al. |
| 8,273,733 B2 | 9/2012 | Diaz Martin et al. |
| 2001/0034352 A1 | 10/2001 | Peglion et al. |
| 2002/0165251 A1 | 11/2002 | Caldirola et al. |
| 2003/0027836 A1 | 2/2003 | Matsui et al. |
| 2005/0043304 A1 | 2/2005 | Kato et al. |
| 2005/0267146 A1 | 12/2005 | Xue et al. |
| 2006/0167023 A1 | 7/2006 | Jolidon et al. |
| 2007/0105834 A1 | 5/2007 | Diaz Martin et al. |
| 2012/0149728 A1 | 6/2012 | Langevin et al. |
| 2012/0323003 A1 | 12/2012 | Diaz Martin et al. |

FOREIGN PATENT DOCUMENTS

| | | |
|---|---|---|
| EP | 0300725 A1 | 1/1989 |
| EP | 1072596 A2 | 1/2001 |
| EP | 1122252 A1 | 8/2001 |
| WO | 94/29273 A1 | 12/1994 |
| WO | 00/07993 A1 | 2/2000 |
| WO | 01/74808 A1 | 10/2001 |
| WO | 02/076925 A2 | 10/2002 |
| WO | 03/055848 A2 | 7/2003 |
| WO | 03/074051 A1 | 9/2003 |
| WO | 2004/094371 A2 | 11/2004 |
| WO | 2005/008037 A1 | 1/2005 |
| WO | 2005/067502 A2 | 7/2005 |
| WO | 2005/070133 A2 | 8/2005 |
| WO | 2005/110409 A2 | 11/2005 |
| WO | 2005/120505 A2 | 12/2005 |
| WO | 2005/123089 A2 | 12/2005 |
| WO | 2006/018308 A1 | 2/2006 |
| WO | 2006/018309 A1 | 2/2006 |
| WO | 2006/024823 A1 | 3/2006 |
| WO | 2006/065216 A1 | 6/2006 |
| WO | 2006/067587 A2 | 6/2006 |
| WO | 2006/068826 A2 | 6/2006 |
| WO | 2006/108879 A2 | 10/2006 |
| WO | 2006/122014 A2 | 11/2006 |
| WO | 2008/043544 A1 | 4/2008 |
| WO | 2008/136378 A1 | 11/2008 |
| WO | 2009/127822 A2 | 10/2009 |
| WO | 2010/127272 A2 | 11/2010 |
| WO | 2010/151611 A1 | 12/2010 |
| WO | 2011/109675 A2 | 9/2011 |
| WO | 2011/109680 A2 | 9/2011 |
| WO | 2005/118547 A1 | 12/2012 |

OTHER PUBLICATIONS

Grunewald G.L. et al., "3,7-Disubstituted-1,2,3,4-Tetrahydroisoquinolines Display Remarkable Potency and Selectivity as Inhibitors of Phenylethanolamine N-Methyltransferase Versus the a2-Adrenoceptor", Journal of Medicinal Chemistry 42(11):1982-1990 (1999).
Giovannini, Maria Grazia et al "Effects of histamine H3 receptor agonists and antagonists on cognitive performance and scopolamine-induced amnesia" Behavioural Brain Research (1999) vol. 104, pp. 147-155.
Blank, Benjamin et al "Inhibitors of Phenylethanolamine N-Methyltransferase and Epinephrine Biosynthesis. 2. 1,2,3,4-Tetrahydroisoquinoline-7-sulfonanilides" Journal of Medicinal Chemistry (1980) vol. 23, pp. 837-840.
Turner, Sean C. et al"A New Class of Histamine H3-Receptor Antagonists: Synthesis and Structure-Activity Relationships of 7,8,9,10-Tetrahydro-6H-cyclohepta[b]quinolines" Bioorganic & Medicinal Chemistry Letters (2003) vol. 13, pp. 2131-2135.
Tang, Guozhi et al "Pyrogallol-Based Molecules as Potent Inhibitors of the Antiapoptotic Bcl-2 Proteins" Journal of Medicinal Chemistry (2007) vol. 50 No. 8, pp. 1723-1726.

(Continued)

*Primary Examiner* — Zinna Northington Davis
(74) *Attorney, Agent, or Firm* — Scully, Scott, Murphy & Presser, P.C.

(57) ABSTRACT

Industrially applicable process for preparing 2-(cyclohexylmethyl)-N-{2-[(2S)-1-methylpyrrolidin-2-yl]ethyl}-1,2,3,4-tetrahydroisoquinoline-7-sulfonamide, and salts thereof.

18 Claims, No Drawings

(56) References Cited

OTHER PUBLICATIONS

Ueno, Hiroshi et al "Synthesis and Structure-Activity Relationships of Novel Selective Factor Xa Inhibitors with a Tetrahydroisoquinoline Ring" Journal of Medicinal Chemistry (2005) vol. 48 No. 10, pp. 3586-3604.

Fish, Paul V. et al "Synthesis of 1,2,5,6-Tetrahydro-3-pyridinylalanine: A Key Intermediate in the Preparation of Thrombin Inhibitor UK-239,326" Synthetic Communications (2008) vol. 38 No. 16, pp. 2787-2798.

DeLucca, George V. et al "Discovery of CC Chemokine Receptor-3 (CCR3) Antagonists with Picomolar Potency" Journal of Medicinal Chemistry ( 2005) vol. 48 No. 15, pp. 4746-4749.

Palani, Anandan et al "Biaryl Ureas as Potent and Orally Efficacious Melanin Concentrating Hormone Receptor 1 Antagonists for the Treatment of Obesity" Journal of Medicinal Chemistry (2005) vol. 48 No. 6, pp. 2194-2211.

Brinner, Kristin M. et al "Potent 4-aminopiperidine based antimalarial agents" Bioorganic & Medicinal Chemistry Letters (2005) vol. 15 No. 2, pp. 345-348.

Grunewald, Gary L. et al "Synthesis, Biochemical Evaluation, and Classical and Three-Dimensional Quantitative Structure-Activity Relationship Studies of 7-Substituted-1,2,3,4-tetrahydroisoquinolines and Their Relative Affinities toward Phenylethanolamine N-Methyltransferase and the a2-Adrenoceptor" Journal of Medicinal Chemistry (1999) vol. 42, pp. 118-134.

Debenneville, Peter L. et al "The Behavior of Aliphatic Aldehydes in the Leuckart-Wallach Reaction" J. Amer. Chem. Soc. (1950) vol. 72, pp. 3073-3075.

Clarke, C. B. et al "Decahydroisoquinolines and Related Compounds. Part II.* Some FurtherExamples of Abnormal Ultraviolet Absorption" Journal of the Chemical Society (1958) pp. 1967-1974.

U.S. Appl. No. 13/600,975, filed Aug. 31, 2012, Entitled: Process for the Preparation of 2-(Cyclohexylmethyl)-N-{2-[(2S)-1-Methylpyrrolidin-2-yl]Ethyl)-1,2,3,4-Tetrahydroisoquinoline-7-Sulfonamide, first named inventor Steven Elenbaas.

Costa Rican Opposition issued in related Costa Rican Patent Application No. 2012-0467, (Jan. 8, 2013).

PROCESS FOR THE PREPARATION OF 2-(CYCLOHEXYLMETHYL)-N-{2-[(2S)-1-METHYLPYRROLIDIN-2-YL]ETHYL}-1,2,3,4-TETRAHYDROISOQUINOLINE-7-SULFONAMIDE

This application is a Continuation of PCT/US2011/027131 filed on Mar. 4, 2011 and claims the benefit of U.S. Provisional Application No. 61/311,069 filed on Mar. 5, 2010, which is hereby incorporated by reference herein in its entirety.

FIELD OF THE INVENTION

The present invention relates to processes for preparing 2-(cyclohexylmethyl)-N-{2-[(2S)-1-methylpyrrolidin-2-yl]ethyl}-1,2,3,4-tetrahydroisoquinoline-7-sulfonamide, various intermediates thereto and pharmaceutically acceptable salts thereof.

BACKGROUND OF THE INVENTION

The histamine H3 receptors are found in the central and peripheral nervous systems. The administration of histamine H3 receptor ligands may influence the secretion of neurotransmitters in the brain and the periphery and thus can be useful in the treatment of several disorders, including Alzheimer's disease and other dementias, obesity, central nervous system disorders such as vigilance and sleep disorders, narcolepsy, Parkinson's disease, attention-deficit hyperactivity disorder, memory and learning disorders, epilepsy, schizophrenia, moderate cognitive disorders, depression, anxiety, cardiovascular disorders, and gastrointestinal disorders.

To illustrate, a number of studies in the literature have demonstrated the cognitive enhancing properties of histamine H3 receptors antagonists in rodent models (See, e.g., Giovanni et al., Behav. Brain Res., 1999, 104, 147-155). These reports further suggest that antagonists and/or inverse agonists could be useful for the treatment of cognitive impairments in neurological diseases such as Alzheimer's disease and related neurodegenerative disorders. Alzheimer's disease is the most common cause of dementia in the elderly, and is often characterized with one or more symptoms such as memory loss, confusion, irritability and aggression, mood swings, language breakdown, long-term memory loss, withdrawal of the sufferer, and loss of motor control.

2-(Cyclohexylmethyl)-N-{2-[(2S)-1-methylpyrrolidin-2-yl]ethyl}-1,2,3,4-tetrahydroisoquinoline-7-sulfonamide, which has the structure of Formula (I):

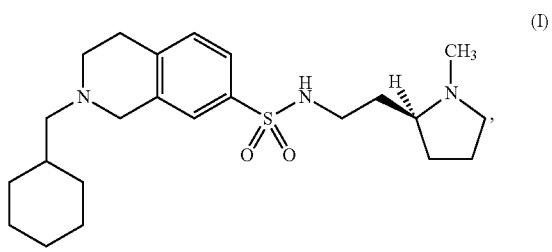 [SMILES: CN1CCC[C@H]1CCNS(=O)(=O)c1ccc2c(c1)CN(CC1CCCCC1)CC2]

(I)

is a potent histamine H3 receptor antagonist with inverse agonist properties. A preparation and the physical properties and beneficial pharmacological properties of 2-(cyclohexylmethyl)-N-{2-[(2S)-1-methylpyrrolidin-2-yl]ethyl}-1,2,3,4-tetrahydroisoquinoline-7-sulfonamide are described in, for example, WO2005/118547 (also US2007/0105834).

WO2005/118547 describes a general method of synthesis which is difficult to transpose to the industrial scale for production in large quantities. This method of synthesis entails reacting 2-(2,2,2-trifluoroacetyl)-1,2,3,4-tetrahydro-isoquinoline-7-sulfonyl chloride with (+/−)-2-(2-aminoethyl)-1-methylpyrrolidine, which product is deprotected in methanol and hydrochloric acid. The enantiomers are next separated by chiral chromatography. The resulting N-{2-[(2S)-1-methylpyrrolidin-2-yl]ethyl}-1,2,3,4-tetrahydroisoquinoline-7-sulfonamide undergoes reductive amination with cyclohexanecarboxaldehyde in the presence of a palladium catalyst. 2-(Cyclohexylmethyl)-N-{2-[(2S)-1-methylpyrrolidin-2-yl]ethyl}-1,2,3,4-tetrahydroisoquinoline-7-sulfonamide is isolated as the free base and converted to a salt.

The present invention makes it possible to optimize the synthesis of 2-(cyclohexylmethyl)-N-{2-[(2S)-1-methylpyrrolidin-2-yl]ethyl}-1,2,3,4-tetrahydroisoquinoline-7-sulfonamide for industrial use by avoiding the chiral chromatographic separation of the enantiomers of (+/−)-N-[2-(1-methylpyrrolidin-2-yl)ethyl]-1,2,3,4-tetrahydroisoquinoline-7-sulfonamide. The present invention deals with the chirality issues first, allowing the coupling of 2-(2,2,2-trifluoroacetyl)-1,2,3,4-tetrahydroisoquinoline-7-sulfonyl chloride with enantiomerically pure (>99% ee) (+)-2-(2-aminoethyl)-1-methylpyrrolidine. In so doing, more of the 1,2,3,4-tetrahydroisquinoline moiety in the starting sulfonyl chloride can be incorporated into product. Using the above-described synthesis, half of this material would have been discarded with the unwanted enantiomer of N-[2-(1-methylpyrrolidin-2-yl)ethyl]-1,2,3,4-tetrahydroisoquinoline-7-sulfonamide.

BRIEF SUMMARY OF THE INVENTION

Accordingly, the present invention provides a process for producing 2-(cyclohexylmethyl)-N-{2-[(2S)-1-methylpyrrolidin-2-yl]ethyl}-1,2,3,4-tetrahydroisoquinoline-7-sulfonamide and salts thereof, of high purity and in a relatively high yield suitable for use on an industrial scale.

The present invention is also directed to synthetic intermediates, for example 2-(2,2,2-trifluoroacetyl)-N-{2-[(2S)-1-methylpyrrolidin-2-yl]ethyl}-1,2,3,4-tetrahydroisoquinoline-7-sulfonamide, a compound of Formula (III), wherein Pg=COCF$_3$, that are useful in the preparation of the 2-(cyclohexylmethyl)-N-{2-[(2S)-1-methylpyrrolidin-2-yl]ethyl}-1,2,3,4-tetrahydroisoquinoline-7-sulfonamide and salts thereof.

DETAILED DESCRIPTION OF THE INVENTION

Definitions and Abbreviations

As used above, and throughout the description of the invention, the following abbreviations, unless otherwise indicated, shall be understood to have the following meanings:

| | |
|---|---|
| HPLC | high performance liquid chromatography |
| kg | kilogram |
| L | liter |
| mL | milliliter |
| MTBE | methyl t-butyl ether |

The term "pharmaceutically acceptable" refers to those compounds, materials, compositions, carrier agents, bulking agents, solvents, diluents and other excipients which are, within the scope of sound medicinal judgment, suitable for contact with humans or other mammals without undue toxicity, irritation, allergic response and the like, commensurate with a reasonable benefit/risk ratio.

A process of the invention for preparing 2-(cyclohexylmethyl)-N-{2-[(2S)-1-methylpyrrolidin-2-yl]ethyl}-1,2,3,4-tetrahydroisoquinoline-7-sulfonamide, or a pharmaceutically acceptable salt thereof, or a solvate or hydrate of a pharmaceutically acceptable salt comprises:

a) coupling (−)-2-(2-aminoethyl)-1-methylpyrrolidine with an amine-protected tetrahydroquinoline-7-sulfonyl chloride to give an amine-protected N-{2-[(2S)-1-methylpyrrolidin-2-yl]ethyl}-1,2,3,4-tetrahydroisoquinoline-7-sulfonamide;

b) deprotecting the amine-protected N-{2-[(2S)-1-methylpyrrolidin-2-yl]ethyl}-1,2,3,4-tetrahydroisoquinoline-7-sulfonamide to give N-{2-[(2S)-1-methylpyrrolidin-2-yl]ethyl}-1,2,3,4-tetrahydroisoquinoline-7-sulfonamide or a salt thereof;

c) reductively aminating N-{2-[(2S)-1-methylpyrrolidin-2-yl]ethyl}-1,2,3,4-tetrahydroisoquinoline-7-sulfonamide or a salt thereof with cyclohexanecarboxaldehyde to form 2-(cyclohexylmethyl)-N-{2-[(2S)-1-methylpyrrolidin-2-yl]ethyl}-1,2,3,4-tetrahydroisoquinoline-7-sulfonamide;

d) optionally reacting 2-(cyclohexylmethyl)-N-{2-[(2S)-1-methylpyrrolidin-2-yl]ethyl}-1,2,3,4-tetrahydroisoquinoline-7-sulfonamide, with a stoichiometric amount or an excess of a salt-forming acid in a solvent to form a salt or a hydrate or solvate thereof; and e) optionally recrystallizing the product of step d).

In one aspect of the invention, processes for preparing the 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt, solvate, or hydrate thereof, or a solvate or hydrate of a pharmaceutically acceptable salt and the intermediates that are useful for preparing such compounds are outlined in Scheme 1:

Scheme 1:

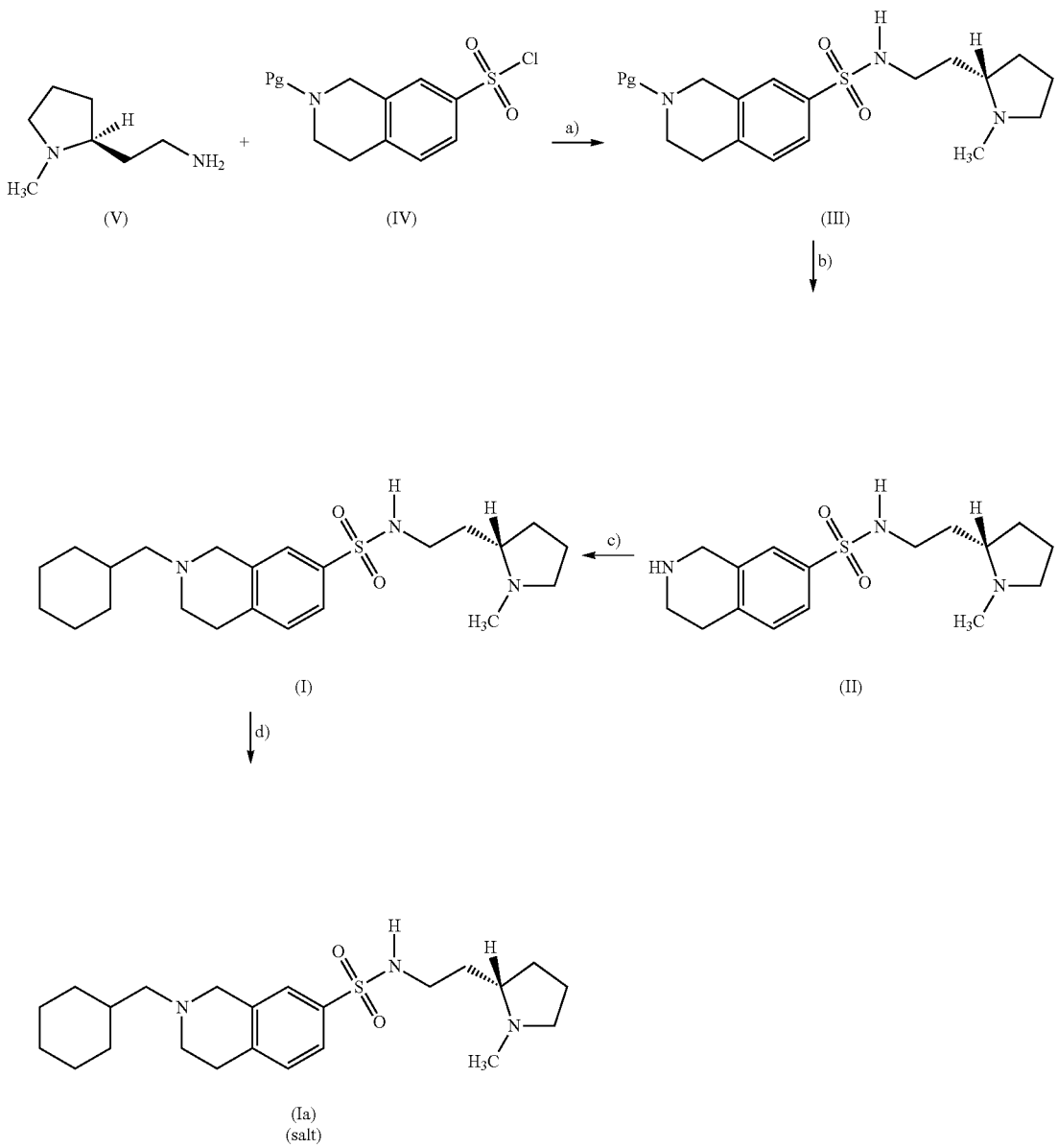

The processes for preparing 2-(cyclohexylmethyl)-N-{2-[(2S)-1-methylpyrrolidin-2-yl]ethyl}-1,2,3,4-tetrahydroisoquinoline-7-sulfonamide, or a pharmaceutically acceptable salt thereof, or a solvate or hydrate of a pharmaceutically acceptable salt, as outlined in Scheme 1, comprise:
a) coupling (−)-2-(2-aminoethyl)-1-methylpyrrolidine with amine-protected tetrahydroquinoline-7-sulfonyl chloride to give a compound of Formula (III), amine-protected N-{2-[(2S)-1-methylpyrrolidin-2-yl]ethyl}-1,2,3,4-tetrahydroisoquinoline-7-sulfonamide, wherein Pg represents an amine protecting group;
b) deprotecting the compound of Formula (III) to give the compound of Formula (II), N-{2-[(2S)-1-methylpyrrolidin-2-yl]ethyl}-1,2,3,4-tetrahydroisoquinoline-7-sulfonamide or a salt thereof;
c) reductively aminating the compound of Formula (II) with cyclohexanecarboxaldehyde to give a compound of Formula (I), 2-(cyclohexylmethyl)-N-{2-[(2S)-1-methylpyrrolidin-2-yl]ethyl}-1,2,3,4-tetrahydroisoquinoline-7-sulfonamide;
d) optionally reacting the compound of Formula (I) with a stoichiometric amount or an excess of a salt-forming acid in a solvent to form a salt, or a hydrate or solvate thereof, of Formula (Ia), 2-(cyclohexylmethyl)-N-{2-[(2S)-1-methylpyrrolidin-2-yl]ethyl}-1,2,3,4-tetrahydroisoquinoline-7-sulfonamide addition salt; and
e) optionally recrystallizing the product of step d).

A particular process of the invention for preparing 2-(cyclohexylmethyl)-N-{2-[(2S)-1-methylpyrrolidin-2-yl]ethyl}-1,2,3,4-tetrahydroisoquinoline-7-sulfonamide, or a pharmaceutically acceptable salt thereof, or a solvate or hydrate of a pharmaceutically acceptable salt, comprises:
a) coupling (−)-2-(2-aminoethyl)-1-methylpyrrolidine with an amine-protected tetrahydroquinoline-7-sulfonyl chloride in the presence of a base to give an amine-protected N-{2-[(2S)-1-methylpyrrolidin-2-yl]ethyl}-1,2,3,4-tetrahydroisoquinoline-7-sulfonamide;
b) deprotecting the amine-protected N-{2-[(2S)-1-methylpyrrolidin-2-yl]ethyl}-1,2,3,4-tetrahydroisoquinoline-7-sulfonamide under basic conditions and in a solvent selected from an alcohol and a combination of water with an ethereal solvent, to give N-{2-[(2S)-1-methylpyrrolidin-2-yl]ethyl}-1,2,3,4-tetrahydroisoquinoline-7-sulfonamide or a salt thereof;
c) reductively aminating N-{2-[(2S)-1-methylpyrrolidin-2-yl]ethyl}-1,2,3,4-tetrahydroisoquinoline-7-sulfonamide or a salt thereof with cyclohexanecarboxaldehyde in the presence of a reducing agent and in a solvent selected from an alcohol and a combination of water with an ethereal solvent, to form 2-(cyclohexylmethyl)-N-{2-[(2S)-1-methylpyrrolidin-2-yl]ethyl}-1,2,3,4-tetrahydroisoquinoline-7-sulfonamide;
d) optionally reacting 2-(cyclohexylmethyl)-N-{2-[(2S)-1-methylpyrrolidin-2-yl]ethyl}-1,2,3,4-tetrahydroisoquinoline-7-sulfonamide, or a hydrate or solvate thereof, with a stoichiometric amount or an excess of a salt-forming acid in a solvent to form a salt or a hydrate or solvate thereof; and
e) optionally recrystallizing the product of step d).

Another particular process of the invention for preparing 2-(cyclohexylmethyl)-N-{2-[(2S)-1-methylpyrrolidin-2-yl]ethyl}-1,2,3,4-tetrahydroisoquinoline-7-sulfonamide, or a pharmaceutically acceptable salt thereof, or a solvate or hydrate of a pharmaceutically acceptable salt, comprises:
a) coupling (−)-2-(2-aminoethyl)-1-methylpyrrolidine with 2-(2,2,2-trifluoroacetyl)-1,2,3,4-tetrahydroquinoline-7-sulfonyl chloride to give 2-(2,2,2-trifluoroacetyl)-N-{2-[(2S)-1-methylpyrrolidin-2-yl]ethyl}-1,2,3,4-tetrahydroisoquinoline-7-sulfonamide;
b) deprotecting 2-(2,2,2-trifluoroacetyl)-N-{2-[(2S)-1-methylpyrrolidin-2-yl]ethyl}-1,2,3,4-tetrahydroisoquinoline-7-sulfonamide to give N-{2-[(2S)-1-methylpyrrolidin-2-yl]ethyl}-1,2,3,4-tetrahydroisoquinoline-7-sulfonamide, or a salt thereof;
c) reductively aminating N-{2-[(2S)-1-methylpyrrolidin-2-yl]ethyl}-1,2,3,4-tetrahydroisoquinoline-7-sulfonamide, or a salt thereof with cyclohexanecarboxaldehyde to form 2-(cyclohexylmethyl)-N-{2-[(2S)-1-methylpyrrolidin-2-yl]ethyl}-1,2,3,4-tetrahydroisoquinoline-7-sulfonamide;
d) optionally reacting 2-(cyclohexylmethyl)-N-{2-[(2S)-1-methylpyrrolidin-2-yl]ethyl}-1,2,3,4-tetrahydroisoquinoline-7-sulfonamide, with a stoichiometric amount or an excess of a salt-forming acid in a solvent to form a salt, or a hydrate or solvate thereof; and
e) optionally recrystallizing the product of step d).

For Scheme 1:
Amine-protected N-{2-[(2S)-1-methylpyrrolidin-2-yl]ethyl}-1,2,3,4-tetrahydroisoquinoline-7-sulfonamide is prepared in step a) from a coupling between (−)-2-(2-aminoethyl)-1-methylpyrrolidine and an amine-protected 1,2,3,4-tetrahydroisoquinoline-7-sulfonyl chloride, such as 2-(2,2,2-trifluoroacetyl)-1,2,3,4-tetrahydroisoquinoline-7-sulfonyl chloride or 1,2,3,4-tetrahydroisoquinoline-7-sulfonyl chloride protected with other suitable amine-protecting groups (i.e., amine-protecting groups that are stable in acid and removable under conditions that would not cleave the sulfonamide bond). In one aspect, 2-(2,2,2-trifluoroacetyl)-N-{2-[(2S)-1-methylpyrrolidin-2-yl]ethyl}-1,2,3,4-tetrahydroisoquinoline-7-sulfonamide is prepared from a coupling between (−)-2-(2-aminoethyl)-1-methylpyrrolidine and 2-(2,2,2-trifluoroacetyl)-1,2,3,4-tetrahydroisoquinoline-7-sulfonyl chloride in the presence of an inorganic base, such as sodium hydroxide, potassium hydroxide, lithium hydroxide, and the like, or an organic base, such as triethylamine and the like; in an inert solvent, for example a halogenated solvent such as dichloromethane, chloroform, 1,2-dichloroethane, and the like, or an ethereal solvent such as t-butyl methyl ether or 2-methyltetrahydrofuran and the like; at temperatures preferably between about 0° C. and ambient temperature, for example about 25° C.

Accordingly, one embodiment of the invention is a process for preparing 2-(2,2,2-trifluoroacetyl)-N-{2-[(2S)-1-methylpyrrolidin-2-yl]ethyl}-1,2,3,4-tetrahydroisoquinoline-7-sulfonamide comprising coupling 2-(2,2,2,-trifluoroacetyl)-1,2,3,4-tetrahydroisoquinoline-7-sulfonyl chloride and (−)-2-(2-aminoethyl)-1-methylpyrrolidine in the presence of a base and in an inert solvent. Another embodiment of the invention is a process for preparing 2-(cyclohexylmethyl)-N-{2-[(2S)-1-methylpyrrolidin-2-yl]ethyl}-1,2,3,4-tetrahydroisoquinoline-7-sulfonamide comprising the step of coupling 2-(2,2,2-trifluoroacetyl)-1,2,3,4-tetrahydroisoquinoline-7-sulfonyl chloride and (−)-2-(2-aminoethyl)-1-methylpyrrolidine in the presence of a base and in an inert solvent.

Amine-protected 1,2,3,4-tetrahydroisoquinoline-7-sulfonyl chloride, such as 2-(2,2,2-trifluoroacetyl)-1,2,3,4-tetrahydroisoquinoline-7-sulfonyl chloride, may be commercially available or otherwise may be prepared according to processes known to those skilled in the art (see, for example, Blank, B.; Krog, A. J.; Weiner, G.; Pendleton, R. G. *J. Med. Chem.* 1980, 23, 837-840). For example, amine-protected 1,2,3,4-tetrahydroisoquinoline-7-sulfonyl chlorides can be prepared by reacting the amine-protected 1,2,3,4-tetrahydroisoquinoline with an excess of chlorosulfonic acid in a halogenated solvent such as dichloromethane, chloroform or 1,2-dichloroethane. In particular, 2-(2,2,2-trifluoroacetyl)-1,2,3,4-tetrahydroisoquinoline-7-sulfonyl chloride can be prepared by reacting 2-(2,2,2-trifluoroacetyl)-1,2,3,4-tetrahydroisoquinoline with excess chlorosulfonic acid in either chloroform or dichloromethane at about 0° C. to about 5° C. for several hours and then at room temperature for several days. Quenching of the reaction into a mixture of chloroform or dichloromethane and crushed ice affords a solution of the desired sulfonyl chloride, which following removal of the solvent, can be purified by crystallization from, for example, t-butyl methyl ether.

The deprotection of amine-protected N-{2-[(2S)-1-methylpyrrolidin-2-yl]ethyl}-1,2,3,4-tetrahydroisoquinoline-7-sulfonamide, such as 2-(2,2,2-trifluoroacetyl)-N-{2-[(2S)-1-methylpyrrolidin-2-yl]ethyl}-1,2,3,4-tetrahydroisoquinoline-7-sulfonamide, in step b) may be carried out using deprotection techniques known in the art. Preferably, the protecting group may be removed under basic conditions, for example in the presence of an inorganic base such as potassium hydroxide, sodium hydroxide, lithium hydroxide, and potassium carbonate. The reaction is preferably carried out in an alcohol, such as isopropanol, methanol, and the like, or combinations of water with an ethereal solvent, such as tetrahydrofuran and dioxane, and at a temperature between about 0° C. and about the reflux temperature of the mixture, and, more preferably, below about 100° C.

Therefore, one embodiment of the invention is the process for preparing N-{2-[(2S)-1-methylpyrrolidin-2-yl]ethyl}-1,2,3,4-tetrahydroisoquinoline-7-sulfonamide comprising deprotecting 2-(2,2,2-trifluoroacetyl)-N-{2-[(2S)-1-methylpyrrolidin-2-yl]ethyl}-1,2,3,4-tetrahydroisoquinoline-7-sulfonamide in the presence of a base. Another embodiment of the invention is the process for preparing 2-(cyclohexylmethyl)-N-{2-[(2S)-1-methylpyrrolidin-2-yl]ethyl}-1,2,3,4-tetrahydroisoquinoline-7-sulfonamide comprising the step of deprotecting 2-(2,2,2-trifluoroacetyl)-N-{2-[(2S)-1-methylpyrrolidin-2-yl]ethyl}-1,2,3,4-tetrahydroisoquinoline-7-sulfonamide in the presence of a base.

Step c) involves the formation of 2-(cyclohexylmethyl)-N-{2-[(2S)-1-methylpyrrolidin-2-yl]ethyl}-1,2,3,4-tetrahydroisoquinoline-7-sulfonamide by reacting N-{2-[(2S)-1-methylpyrrolidin-2-yl]ethyl}-1,2,3,4-tetrahydroisoquinoline-7-sulfonamide and cyclohexanecarboxaldehyde, in the presence of a reducing agent, such as formic acid (produced by the addition of sodium or potassium formate, and the like, for example) in an organic solvent, for example an alcohol, such as ethanol, methanol, isopropanol, and the like, or a combination of water with an ethereal solvent, such as tetrahydrofuran, dioxane, and the like, or a combination of acetonitrile with water or an alcohol with water. This reaction is preferably performed at temperatures between about 0° C. and about the reflux temperature of the mixture, and, more preferably, below about 100° C.

Pharmaceutically acceptable salts of 2-(cyclohexylmethyl)-N-{2-[(2S)-1-methylpyrrolidin-2-yl]ethyl}-1,2,3,4-tetrahydroisoquinoline-7-sulfonamide, and hydrates and solvates thereof, include conventional, non-toxic salts of 2-(cyclohexylmethyl)-N-{2-[(2S)-1-methylpyrrolidin-2-yl]ethyl}-1,2,3,4-tetrahydroisoquinoline-7-sulfonamide, which can be formed with either inorganic acids such as hydrochloric acid or organic acids such as benzoic acid, fumaric acid, oxalic acid and L-tartaric acid. A pharmaceutically acceptable salt can be obtained using standard procedures well known in the art, such as by reacting the compound of Formula (I) with stoichiometric amounts or with an excess of the desired salt-forming acid in a suitable solvent or various combinations of solvents. For example, an oxalate salt can be made by dissolving the compound of Formula (I) in ethanol and adding about 1.1 equivalents of oxalic acid, and allowing the salt to form. In one aspect of the invention, a fumarate salt is obtained. In a preferred aspect, the fumarate salt is a difumarate monohydrate salt.

The pharmaceutically acceptable salt of 2-(cyclohexylmethyl)-N-{2-[(2S)-1-methylpyrrolidin-2-yl]ethyl}-1,2,3,4-tetrahydroisoquinoline-7-sulfonamide, or hydrate or solvate thereof, is optionally recrystallized. Suitable recrystallization solvents include, for example, isopropanol and ethanol in the presence of an antisolvent such as toluene or acetone.

Another aspect of the invention are the processes described above further comprising the step of formulating 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof, or a solvate or hydrate of a pharmaceutically acceptable salt, with one or more pharmaceutically acceptable carrier agents, bulking agents, solvents, diluents and other excipients. In one aspect, the process comprises the step of formulating 2-(cyclohexylmethyl)-N-{2-[(2S)-1-methylpyrrolidin-2-yl]ethyl}-1,2,3,4-tetrahydroisoquinoline-7-sulfonamide difumarate monohydrate with one or more pharmaceutically acceptable carrier agents, bulking agents, solvents, diluents and other excipients.

The compound of Formula (V), (−)-2-(2-aminoethyl)-1-methylpyrrolidine, may be prepared as outlined in Scheme 2.

Scheme 2:

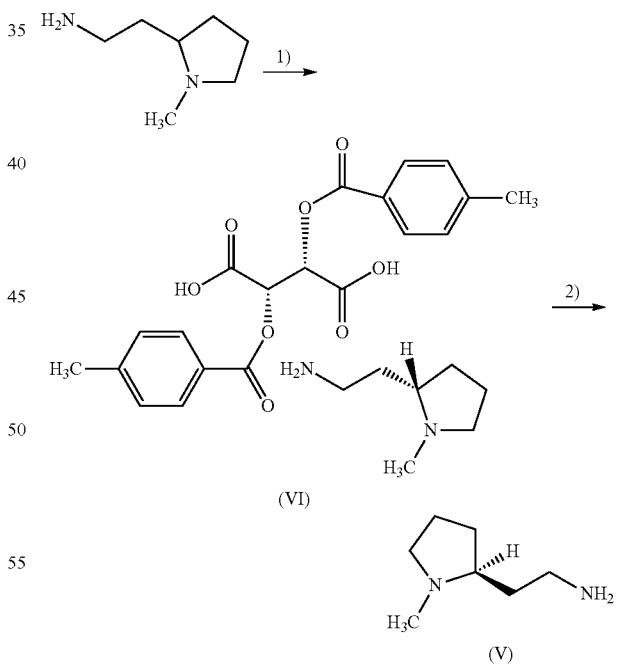

For Scheme 2:

Step 1) entails combining 2-(2-aminoethyl)-1-methylpyrrolidine with a chiral resolving agent, such as di-p-toluoyl-D-tartaric acid, in an alcohol, such as ethanol, methanol, isopropanol, and the like, and combinations thereof including combinations with water. Preferably, the solvent is a combination of ethanol and water. The reaction is preferably performed at temperatures between about 0° C. and about the reflux temperature of the mixture, and more preferably, below about 100° C.

Racemic 2-(2-aminoethyl)-1-methylpyrrolidine starting material is commercially available (for example, from Anichem LLC, American Custom Chemicals Inc., Acros, Aldrich) or otherwise may be prepared according to procedures well known to those skilled in the art. (See Turner, S. C.; Esbenshade, T. A.; Bennani, Y. L.; Hancock, A. A. *Bioorg. Med. Chem. Lett.* 2003, 13, 2131-2135).

Step 2) involves removing the resolving agent by dissolving the product of step 1), for example, (−)-2-(2-aminoethyl)-1-methylpyrrolidine, O,O' di-p-toluoyl-D-tartaric acid salt, in a two-phase mixture of a strong acid, such as concentrated HCl, HBr, $H_2SO_4$, or $H_3PO_4$, and a non-polar solvent, such as t-butyl methyl ether, isopropyl acetate, and the like, at temperatures between about room temperature and about 100° C. In one aspect, (−)-2-(2-aminoethyl)-1-methylpyrrolidine is isolated in aqueous solution as a salt. In another aspect, the acidic solution of (−)-2-(2-aminoethyl)-1-methylpyrrolidine salt is basified by the addition of a base, such as sodium hydroxide, allowing the isolation of (−)-2-(2-aminoethyl)-1-methylpyrrolidine as the distillable free base.

The following examples present typical syntheses as described in Schemes 1 and 2. These examples are understood to be illustrative only and are not intended to limit the scope of the present invention in any way.

Example 1

Preparation of Compound of Formula (VI)

(−)-2-(2-Aminoethyl)-1-methylpyrrolidine, O,O'-Di-p-toluoyl-D-tartaric acid salt A stock solution of aqueous ethanol was prepared by mixing ethanol (10370 mL) and water (2080 mL). A mixture of O,O'-di-p-tolouyl-D-tartaric acid (1624 g, 4.203 mol) and a portion of the above-described stock solution of aqueous ethanol (9050 mL) was stirred at around 65° C. under a nitrogen atmosphere. Separately, racemic 2-(2-aminoethyl)-1-methylpyrrolidine (700 g, 5.35 mol) was dissolved in a portion of the aqueous ethanol stock solution (3400 mL). The amine solution was then added drop-wise to the tartaric acid solution so that the temperature was maintained at about 65° C. and no solids formed during the addition. The reaction was held at about 65° C. for no less than 30 min before being cooled to about 0° C. The precipitate was collected by filtration. A stream of nitrogen was pulled through the collected solid until no longer wet. The solid was recrystallized from ethanol (15950 mL)/water (2457 mL) affording the desired product as a colorless solid: 1322.4 g (44%), >99.5% ee.

Example 2

Preparation of Compound of Formula (V)

(−)-2-(2-Aminoethyl)-1-methylpyrrolidine

A solution of HCl (296 mL, 3.55 mol) and water (517 mL) was added to a mixture of (−)-2-(2-aminoethyl)-1-methylpyrrolidine, O,O'-di-p-toluoyl-D-tartaric acid salt (900 g, 1.75 mol) and MTBE (3.2 L). After stirring for 45 minutes, the layers were separated. Additional MTBE (1.6 L) was added to the aqueous layer. After stirring for about 10 minutes, the layers were separated. With stirring, 50% aqueous NaOH (476 mL, 9.19 mol) was added to the aqueous acid layer over about 35 minutes. The mixture was stirred for about 35 minutes, then cooled to 10° C. The organic layer was separated and distilled at reduced pressure to provided 206 g (92%) of the desired product.

Example 3

Preparation of Compound of Formula (III)

2-(2,2,2-Trifluoroacetyl)-N-{2-[(2S)-1-methylpyrrolidin-2-yl]ethyl}-1,2,3,4-tetrahydroisoquinoline-7-sulfonamide A solution of (−)-2-(2-aminoethyl)-1-methylpyrrolidine (172 g, 1.345 mol) in water (400 mL) was prepared and added to a solution of 2-(2,2,2-trifluoroacetyl)-1,2,3,4-tetrahydroisoquinoline-7-sulfonyl chloride (400 g, 1.22 mol) in 2-methyltetrahydrofuran (1600 mL) at a controlled rate to maintain the reaction temperature between −5° C. and 5° C. Upon completion of the coupling, the reaction mixture was washed once with an aqueous potassium carbonate solution prepared from potassium carbonate (220 g, 1.59 mol) and water (1 L) to liberate the free base of the product. Most of the 2-methyltetrahydrofuran was removed by vacuum distillation to the minimum stirred volume and replaced with ethanol (2 L). The distillation was resumed and continued to the minimum stirred volume. The ethanolic solution of 2-(2,2,2-trifluoroacetyl)-N-{2-[(2S)-1-methylpyrrolidin-2yl]ethyl}-1,2,3,4-tetrahydroisoquinoline-7-sulfonamide was diluted with ethanol (1132 mL) to obtain a 30 wt % solution of product, assuming a 97% yield, and carried forward into the next step.

Example 4

Preparation of a Compound of Formula (II)

N-{2-[(2S)-1-Methylpyrrolidin-2-yl]ethyl}-1,2,3,4-tetrahydroisoquinoline-7-sulfonamide Dihydrochloride Sesquihydrate A 45.7% solution of potassium hydroxide (105 g, 0.855 mol) was added to a 30.66% (w/w) ethanolic solution of 2-(2,2,2-trifluoroacetyl)-N-{2-[(2S)-1-methylpyrrolidin-2-yl]ethyl}-1,2,3,4-tetrahydroisoquinoline-7-sulfonamide (1023.6, 0.748 mol) at a rate that limited the temperature to no more than 45° C. After cooling to room temperature, the reaction was monitored by HPLC. Upon completion of the deprotection, the reaction was acidified by the dropwise addition of concentrated hydrochloric acid (194 mL, 2.35 mol). The precipitated KCl was removed by filtration at between 39-51° C. The reactor was rinsed with ethanol (300 mL) which in turn was used to rinse the collected KCl. The ethanol filtrates were combined and returned to the reactor. The reactor was heated to approximately 55° C. and 2-methyltetrahydrofuran (375 mL) was added. Seed crystals of N-{2-[(2S)-1-methylpyrrolidin-2-yl]ethyl}-1,2,3,4-tetrahydroisoquinoline-7-sulfonamide dihydrochloride sesquihydrate (1 g) were added. After cooling to approximately −5° C., the product was collected by filtration. The product was rinsed with a solution prepared from 2-methyltetrahydrofuran (200 mL), ethanol (200 mL) and water (5 mL). Following drying in a vacuum oven at 40° C., 277 g (87%) of N-{2-[(2S)-1-methylpyrrolidin-2-yl]ethyl}-1,2,3,4-tetrahydroisoquinoline-7-sulfonamide dihydrochloride sesquihydrate was isolated as a colorless solid.

Seed crystals of N-{2-[(2S)-1-Methylpyrrolidin-2-yl]ethyl}-1,2,3,4-tetrahydroisoquinoline-7-sulfonamide dihydrochloride sesquihydrate can be obtained following general procedures known to those skilled in the art. Alternatively, N-{2-[(2S)-1-Methylpyrrolidin-2-yl]ethyl}-1,2,3,4-tetrahydroisoquinoline-7-sulfonamide dihydrochloride sesquihydrate can readily be prepared as described above without the use of seed crystals.

Example 5

Preparation of a Compound of Formula (I)

2-(Cyclohexylmethyl)-N-{2-[(2S)-1-methylpyrrolidin-2-yl]ethyl}-1,2,3,4-tetrahydroisoquinoline-7-sulfonamide N-{2-[(2S)-1-Methylpyrrolidin-2-yl]ethyl}-1,2,3,4-tetrahydroisoquinoline-7-sulfonamide dihydrochloride sesquihydrate (92 g, 0.217 mol) was reacted with potassium formate (33.6 g, 0.399 mol) and cyclohexanecarboxaldehyde (39 mL, 0.322 mol) in hot SDA 3C ethanol (460 mL). The reaction vessel was heated to about 72° C., with release of $CO_2$. The reaction mixture was monitored for completion by HPLC. Upon completion, the reaction was cooled to about 25° C., and ethanol was removed by vacuum distillation and azeotropic removal with added water (280 mL). The hydrochloride salt of the product was formed by the addition of concentrated hydrochloric acid (37.3 mL, 0.451 mol), and the aqueous solution was washed with isopropyl acetate (280 mL). The aqueous layer was basified with a solution of potassium carbonate (92 g, 0.666 mol) in water (100 mL). The aqueous alkaline solution was extracted with isopropyl acetate (460 mL). The isopropyl acetate layer was washed with water (3×460 mL), and the isopropyl acetate was removed by vacuum distillation and replaced with SDA 3C ethanol (460 mL). The resulting clear yellow-tinged solution contained 85.7 g (91%) of 2-(cyclohexylmethyl)-N-{2-[(2S)-1-methylpyrrolidin-2-yl]ethyl}-1,2,3,4-tetrahydroisoquinoline-7-sulfonamide in 120.4 g of solution.

Example 6

Preparation of a Compound of Formula (Ia)

2-(Cyclohexylmethyl)-N-{2-[(2S)-1-methylpyrrolidin-2-yl]ethyl}-1,2,3,4-tetrahydroisoquinoline-7-sulfonamide difumarate monohydrate A solution of 2-(cyclohexylmethyl)-N-{2-[(2S)-1-methylpyrrolidin-2-yl]ethyl}-1,2,3,4-tetrahydroisoquinoline-7-sulfonamide (532 g, 1.27 mol) in SDA 3C ethanol (1056 mL) was added to a suspension of fumaric acid (302 g, 2.60 mol) in water (624 mL). The resulting solution was diluted with acetone (4 L) then cooled and seeded with milled 2-(cyclohexylmethyl)-N-{2-[(2S)-1-methylpyrrolidin-2-yl]ethyl}-1,2,3,4-tetrahydroisoquinoline-7-sulfonamide difumarate monohydrate (4.2 g). After seeding, the mixture was stirred to allow crystal growth then further diluted with acetone (1990 mL). After cooling, the product was collected by filtration and washed with acetone (1.500 L). Filtration was conducted by portionwise loading of acetone into the filter-dryer. After loading of each portion of acetone (1.5 L), stirring was turned on at 2.6 rpm to ensure good contact between product and acetone. The product was dried in a vacuum oven at 40° C. with nitrogen purge and vacuum (residual pressure 400 mBar), then allowed to re-hydrate at room temperature in the air to yield 684.7 g (85.8%) of 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

Seed crystals of 2-(cyclohexylmethyl)-N-{2-[(2S)-1-methylpyrrolidin-2-yl]ethyl}-1,2,3,4-tetrahydroisoquinoline-7-sulfonamide difumarate monohydrate can be obtained following general procedures known to those skilled in the art in view of the above-described procedure. Alternatively, 2-(cyclohexylmethyl)-N-{2-[(2S)-1-methylpyrrolidin-2-yl]ethyl}-1,2,3,4-tetrahydroisoquinoline-7-sulfonamide difumarate monohydrate can readily be prepared as described above without the use of seed crystals.

What is claimed is:

1. A process for preparing 2-(cyclohexylmethyl)-N-{2-[(2S)-1-methylpyrrolidin-2-yl]ethyl}-1,2,3,4-tetrahydroisoquinoline-7-sulfonamide, or a pharmaceutically acceptable salt thereof, or a solvate or hydrate of a pharmaceutically acceptable salt comprising:
   a) coupling (−)-2-(2-aminoethyl)-1-methylpyrrolidine with an amine-protected tetrahydroquinoline-7-sulfonyl chloride to give an amine-protected N-{2-[(2S)-1-methylpyrrolidin-2-yl]ethyl}-1,2,3,4-tetrahydroisoquinoline-7-sulfonamide;
   b) deprotecting the amine-protected N-{2-[(2S)-1-methylpyrrolidin-2-yl]ethyl}-1,2,3,4-tetrahydroisoquinoline-7-sulfonamide to give N-{2-[(2S)-1-methylpyrrolidin-2-yl]ethyl}-1,2,3,4-tetrahydroisoquinoline-7-sulfonamide or a salt thereof;
   c) reductively aminating N-{2-[(2S)-1-methylpyrrolidin-2-yl]ethyl}-1,2,3,4-tetrahydroisoquinoline-7-sulfonamide or a salt thereof with cyclohexanecarboxaldehyde to form 2-(cyclohexylmethyl)-N-{2-[(2S)-1-methylpyrrolidin-2-yl]ethyl}-1,2,3,4-tetrahydroisoquinoline-7-sulfonamide;
   d) optionally reacting 2-(cyclohexylmethyl)-N-{2-[(2S)-1-methylpyrrolidin-2-yl]ethyl}-1,2,3,4-tetrahydroisoquinoline-7-sulfonamide, or a hydrate or solvate thereof, with a stoichiometric amount or an excess of a salt-forming acid in a solvent to form a salt or a hydrate or solvate thereof; and
   e) optionally recrystallizing the product of step d).

2. The process according to claim 1, wherein the amine-protected tetrahydroquinoline-7-sulfonyl chloride is 2-(2,2,2-trifluoroacetyl)-1,2,3,4-tetrahydroisoquinoline-7-sulfonyl chloride and the amine-protected N-{2-[(2S)-1-methylpyrrolidin-2-yl]ethyl}-1,2,3,4-tetrahydroisoquinoline-7-sulfonamide is 2-(2,2,2-trifluoroacetyl)-N-{2-[(2S)-1-methylpyrrolidin-2-yl]ethyl}-1,2,3,4-tetrahydroisoquinoline-7-sulfonamide.

3. The process according to claim 1, wherein the coupling in step a) is performed in the presence of an inorganic or organic base and in an inert solvent.

4. The process according to claim 3, wherein the base is selected from the group consisting of sodium hydroxide, potassium hydroxide, lithium hydroxide and triethylamine.

5. The process according to claim 1, wherein deprotecting in step b) is performed under basic conditions and in an alcohol.

6. The process according to claim 1, wherein the reductive amination of step c) is performed in an organic solvent in the presence of a reducing agent.

7. The process according to claim 6, wherein the reducing agent is formic acid.

8. The process according to claim 1, wherein the salt formed in step d) is a pharmaceutically acceptable salt.

9. The process according to claim 1, further comprising formulating 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof, or a solvate or hydrate of a pharmaceutically acceptable salt, with one or more pharmaceutically acceptable carrier agents, bulking agents, solvents, diluents and other excipients.

10. The process according to claim 1, wherein the salt-forming acid in step d) is fumaric acid to provide 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

11. The process according to claim 10, further comprising formulating 2-(cyclohexylmethyl)-N-{2-[(2S)-1-methylpyrrolidin-2-yl]ethyl}-1,2,3,4-tetrahydroisoquinoline-7-sulfonamide difumarate monohydrate with one or more pharmaceutically acceptable carrier agents, bulking agents, solvents, diluents and other excipients.

12. The process according to claim 1, comprising:
   a) coupling (−)-2-(2-aminoethyl)-1-methylpyrrolidine with 2-(2,2,2-trifluoroacetyl)-1,2,3,4-tetrahydroquinoline-7-sulfonyl chloride to give 2-(2,2,2-trifluoroacetyl)-N-{2-[(2S)-1-methylpyrrolidin-2-yl]ethyl}-1,2,3,4-tetrahydroisoquinoline-7-sulfonamide;
   b) deprotecting 2-(2,2,2-trifluoroacetyl)-N-{2-[(2S)-1-methylpyrrolidin-2-yl]ethyl}-1,2,3,4-tetrahydroisoquinoline-7-sulfonamide to give N-{2-[(2S)-1-methylpyrrolidin-2-yl]ethyl}-1,2,3,4-tetrahydroisoquinoline-7-sulfonamide, or a salt thereof;
   c) reductively aminating N-{2-[(2S)-1-methylpyrrolidin-2-yl]ethyl}-1,2,3,4-tetrahydroisoquinoline-7-sulfonamide, or a salt thereof with cyclohexanecarboxaldehyde to form 2-(cyclohexylmethyl)-N-{2-[(2S)-1-methylpyrrolidin-2-yl]ethyl}-1,2,3,4-tetrahydroisoquinoline-7-sulfonamide;
   d) optionally reacting 2-(cyclohexylmethyl)-N-{2-[(2S)-1-methylpyrrolidin-2-yl]ethyl}-1,2,3,4-tetrahydroisoquinoline-7-sulfonamide with a stoichiometric amount or an excess of a salt-forming acid in a solvent to form a salt, or a hydrate or solvate thereof; and
   e) optionally recrystallizing the product of step d).

13. The process according to claim 12, further comprising formulating 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt, or a solvate or hydrate of a pharmaceutically acceptable salt, with one or more pharmaceutically acceptable carrier agents, bulking agents, solvents, diluents and other excipients.

14. The process according to claim 12, wherein the salt-forming acid in step d) is fumaric acid to provide 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

15. The process according to claim 14, further comprising formulating 2-(cyclohexylmethyl)-N-{2-[(2S)-1-methylpyrrolidin-2-yl]ethyl}-1,2,3,4-tetrahydroisoquinoline-7-sulfonamide difumarate monohydrate with one or more pharmaceutically acceptable carrier agents, bulking agents, solvents, diluents and other excipients.

16. The process according to claim 1, comprising:
   a) coupling (−)-2-(2-aminoethyl)-1-methylpyrrolidine with an amine-protected tetrahydroquinoline-7-sulfonyl chloride in the presence of a base to give an amine-protected N-{2-[(2S)-1-methylpyrrolidin-2-yl]ethyl}-1,2,3,4-tetrahydroisoquinoline-7-sulfonamide;
   b) deprotecting the amine-protected N-{2-[(2S)-1-methylpyrrolidin-2-yl]ethyl}-1,2,3,4-tetrahydroisoquinoline-7-sulfona under basic conditions and in a solvent selected from an alcohol and a combination of water with an ethereal solvent, to give N-{2-[(2S)-1-methylpyrrolidin-2-yl]ethyl}-1,2,3,4-tetrahydroisoquinoline-7-sulfonamide or a salt thereof;
   c) reductively aminating N-{2-[(2S)-1-methylpyrrolidin-2-yl]ethyl}-1,2,3,4-tetrahydroisoquinoline-7-sulfonamide or a salt thereof with cyclohexanecarboxaldehyde in the presence of a reducing agent and in a solvent selected from an alcohol and a combination of water with an ethereal solvent, to form 2-(cyclohexylmethyl)-N-{2-[(2S)-1-methylpyrrolidin-2-yl]ethyl}-1,2,3,4-tetrahydroisoquinoline-7-sulfonamide,
   d) optionally reacting 2-(cyclohexylmethyl)-N-{2-[(2S)-1-methylpyrrolidin-2-yl]ethyl}-1,2,3,4-tetrahydroisoquinoline-7-sulfonamide with a stoichiometric amount or an excess of a salt-forming acid in a solvent to form a salt or a hydrate or solvate thereof; and
   e) optionally recrystallizing the product of step d).

17. A process for preparing 2-(cyclohexylmethyl)-N-{2-[(2S)-1-methylpyrrolidin-2-yl]ethyl}-1,2,3,4-tetrahydroisoquinoline-7-sulfonamide, comprising the step of coupling 2-(2,2,2-trifluoroacetyl)-1,2,3,4-tetrahydroisoquinoline-7-sulfonyl chloride and (−)-2-(2-aminoethyl)-1-methylpyrrolidine in the presence of a base and in an inert solvent.

18. A process for preparing 2-(cyclohexylmethyl)-N-{2-[(2S)-1-methylpyrrolidin-2-yl]ethyl}-1,2,3,4-tetrahydroisoquinoline-7-sulfonamide, comprising the step of deprotecting 2-(2,2,2-trifluoroacetyl)-N-{2-[(2S)-1-methylpyrrolidin-2-yl]ethyl}-1,2,3,4-tetrahydroisoquinoline-7-sulfonamide in the presence of a base.

* * * * *